(12) United States Patent
Nomura

(10) Patent No.: US 10,119,111 B2
(45) Date of Patent: Nov. 6, 2018

(54) CELL COLONY AREA SPECIFYING APPARATUS, CELL COLONY AREA SPECIFYING METHOD, AND RECORDING MEDIUM

(71) Applicant: SCREEN Holdings Co., Ltd., Kyoto (JP)

(72) Inventor: Akihiro Nomura, Kyoto (JP)

(73) Assignee: SCREEN HOLDINGS CO., LTD., Kyoto (JP)

( * ) Notice: Subject to any disclaimer, the term of this patent is extended or adjusted under 35 U.S.C. 154(b) by 219 days.

(21) Appl. No.: 15/111,316

(22) PCT Filed: Nov. 19, 2014

(86) PCT No.: PCT/JP2014/080620
§ 371 (c)(1),
(2) Date: Jul. 13, 2016

(87) PCT Pub. No.: WO2015/107770
PCT Pub. Date: Jul. 23, 2015

(65) Prior Publication Data
US 2016/0348057 A1 Dec. 1, 2016

(30) Foreign Application Priority Data

Jan. 14, 2014 (JP) .................................. 2014-004079
Jan. 14, 2014 (JP) .................................. 2014-004080

(51) Int. Cl.
*C12M 1/34* (2006.01)
*G06T 7/12* (2017.01)
(Continued)

(52) U.S. Cl.
CPC ............ *C12M 41/36* (2013.01); *C12M 41/48* (2013.01); *G06K 9/0014* (2013.01); *G06T 7/12* (2017.01);
(Continued)

(58) Field of Classification Search
CPC ......... C12M 41/36; C12M 41/48; G06T 7/12; G06T 7/155; G06T 7/181; G06T 7/62
See application file for complete search history.

(56) References Cited

U.S. PATENT DOCUMENTS

| 4,769,776 A | 9/1988 | Hiraoka et al. |
| 7,116,447 B2 * | 10/2006 | Braun ................. H04N 1/4055 358/3.12 |

(Continued)

FOREIGN PATENT DOCUMENTS

| JP | 62-50606 A | 3/1987 |
| JP | 62-50607 A | 3/1987 |

(Continued)

OTHER PUBLICATIONS

Ma et al. ("A Simple Way to Realize the Accurate Detection of Cells' Edge," International Conference of Information Technology, Computer Engineering and Management Sciences, Sep. 24-25, 2011) (Year: 2011).*

(Continued)

*Primary Examiner* — Yubin Hung
(74) *Attorney, Agent, or Firm* — McDermott, Will & Emery LLP

(57) ABSTRACT

By deleting a small area from an initial boundary image, a provisional boundary image is obtained (Step S211). A thinning processing is performed on the provisional boundary image to shape the image, and a thickening processing is performed on the thinned image to obtain a mask image (Steps S212 to S214). By masking the initial boundary image with the mask image, an updated provisional boundary image is obtained (Step S215). In the updated provisional boundary image, end points adjacent to each other are connected (Step S216). By repeating Steps S212 to S216, a broken boundary is repaired. As a result, even if a boundary (Continued)

of a cell colony is blurred, an area of the cell colony can be specified easily and efficiently.

27 Claims, 19 Drawing Sheets

(51) Int. Cl.
    *G06T 7/62*     (2017.01)
    *G06K 9/00*     (2006.01)
    *C12M 1/36*     (2006.01)

(52) U.S. Cl.
    CPC ...... *G06T 7/62* (2017.01); *G06T 2207/10056* (2013.01); *G06T 2207/30024* (2013.01)

(56) References Cited

U.S. PATENT DOCUMENTS

| | | | | |
|---|---|---|---|---|
| 2002/0057428 | A1* | 5/2002 | Nakayama | G01M 11/0264 356/239.2 |
| 2003/0179916 | A1* | 9/2003 | Magnuson | C12Q 1/24 382/128 |
| 2005/0053268 | A1* | 3/2005 | Breen | G01N 27/44721 382/128 |
| 2006/0008118 | A1* | 1/2006 | Matsuoka | G06K 9/00711 382/103 |
| 2011/0019897 | A1 | 1/2011 | Takagi et al. | |
| 2012/0114219 | A1 | 5/2012 | Nakagawa et al. | |
| 2012/0250974 | A1* | 10/2012 | Miyamoto | A61B 6/481 382/132 |
| 2014/0126784 | A1* | 5/2014 | Hsieh | G06T 11/005 382/128 |
| 2014/0198852 | A1* | 7/2014 | Incesu | H04N 19/00684 375/240.16 |
| 2014/0363085 | A1* | 12/2014 | Li | G06K 9/00624 382/190 |
| 2016/0321809 | A1* | 11/2016 | Chukka | G06K 9/0014 |

FOREIGN PATENT DOCUMENTS

| | | | |
|---|---|---|---|
| JP | 05225336 A | * | 9/1993 |
| JP | 2007-020507 A | | 2/2007 |
| JP | 2011-024485 A | | 2/2011 |
| JP | 2013-201909 A | | 10/2013 |
| WO | 2011/010449 A1 | | 1/2011 |

OTHER PUBLICATIONS

Nedzved et al. ("Morphological segmentation of histology cell images," Proceedings of the 15th International Conference on Pattern Recognition, Sep. 3-7, 2000) (Year: 2000).*
International Search Report issued in International Application No. PCT/JP2014/080620, dated Feb. 24, 2015, with English Translation.
International Preliminary Report on Patentability issued in International Application No. PCT/JP2014/080620, dated Jul. 28, 2016, with English Translation.

* cited by examiner

613

612

613

614

621

622

622

623

621

621

621

622

622

641

642

643

642

643

644

645

646

647

651

CELL COLONY AREA SPECIFYING APPARATUS, CELL COLONY AREA SPECIFYING METHOD, AND RECORDING MEDIUM

RELATED APPLICATIONS

This application is the U.S. National Phase under 35 U.S.C. § 371 of International Application No. PCT/JP2014/080620, filed on Nov. 19, 2014, which in turn claims the benefit of Japanese Application No. 2014-004079, filed on Jan. 14, 2014, and Japanese Application No. 2014-004080, filed on Jan. 14, 2014, the disclosures of which Applications are incorporated by reference herein.

TECHNICAL FIELD

The present invention relates to a technique for specifying an area of a cell colony in an image obtained by picking up an image of the cell colony which is obtained by culturing a cell.

BACKGROUND ART

In various fields, such as medical care, foods, materials, and the like, conventionally, a technique for culturing cells has been used. In a cell culture, in most cases, formed are colonies in each of which cells are clustered. In a case where many cells are cultured, it is required to analyze images obtained by imaging colonies, to thereby automatically specify only necessary colonies.

In an image processing apparatus disclosed in WO 2011/010449 (Document 1), for example, a user designates a candidate for an iPS cell colony from a synthetic macro image which is a phase contrast microscope image of a culture vessel. By binarizing the synthetic macro image, a binarized colony image is obtained, and from the binarized colony image, a contour line of the designated cell colony is extracted. After that, it is determined whether each cell colony is an iPS cell or not from its feature value.

Also in a cell image analysis apparatus disclosed in Japanese Patent Application Laid Open Gazette No. 2011-24485 (Document 2), a boundary element of an object is extracted by using its luminance and/or luminance difference. At that time, in a case where parts of the boundary element are separated since the amount of variation in the luminance and/or luminance difference is small, the boundary elements which are away from each other at a distance not larger than a predetermined value are identified as those of the same object, and these boundary elements are connected with line segment elements.

In Document 1, since the cell colony which has a clear contour line and is clearly distinguished from the background is designated by the user, it is relatively easy to extract the contour line of the cell colony. In Document 2, though it is considered that there are breaks in the boundary line due to noises or the like, it is not assumed that there is a condition where the boundary is blurred and thickened. In a case where the boundary is blurred due to imaging blur or misfocus, the contour is apt to be wrongly detected.

SUMMARY OF INVENTION

The present invention is intended for a cell colony area specifying apparatus for specifying an area of a cell colony in a colony image representing the cell colony, and it is an object of the present invention to easily and efficiently specify an area of a cell colony even if a boundary of the cell colony is blurred.

A cell colony area specifying apparatus according to the present invention includes an image pickup part for picking up an image of a cell colony, to acquire a colony image, an operation part for specifying an area of the cell colony in the colony image by performing a computation processing, and an output part for outputting the area which is specified.

The operation part performs a) obtaining an initial boundary image provisionally representing a boundary of a cell colony from the colony image, b) acquiring a provisional boundary image by deleting a small area from the initial boundary image, c) obtaining a provisional boundary thin-line image by performing a thinning processing on the provisional boundary image, d) obtaining a mask image by performing a thickening processing on the provisional boundary thin-line image, e) obtaining an updated provisional boundary image by masking the initial boundary image with the mask image, f) connecting end points adjacent to each other in the updated provisional boundary image, g) checking whether a predetermined repeat end condition is satisfied or not after the operation e) and before or after the operation f), and returning to the operation c) after the operation f) when the repeat end condition is not satisfied, or obtaining a boundary thin-line image from an image obtained after the operation f) and going to an operation h) when the repeat end condition is satisfied, and h) specifying an area surrounded by a line in the boundary thin-line image, as an area of a cell colony.

In a preferred embodiment of the present invention, the repeat end condition is that the number of executions of the operation e) or the operation f) reaches a predetermined number or that an image obtained after the operation e) is coincident with an image obtained after a previous operation e).

In another preferred embodiment of the present invention, after the operation g) and before the operation h), when a ratio of a distance between both ends of a line which is not annular to a length of the line in the boundary thin-line image is not larger than a predetermined value, the operation part further performs connecting the both ends.

In still another preferred embodiment of the present invention, when a difference in average lightness between the inside of the area surrounded by the line in the boundary thin-line image and a peripheral portion of the area is not larger than a predetermined value in the colony image, the operation h) includes determining the area not as an area of a cell colony.

Another cell colony area specifying apparatus according to the present invention includes an image pickup part for picking up an image of a cell colony, to acquire a colony image, an operation part for specifying an area of the cell colony in the colony image by performing a computation processing, and an output part for outputting the area which is specified. The operation part performs a) obtaining a lightness change image representing a difference in lightness between each position in the colony image and its periphery, b) obtaining a lightness change binary image by binarizing the lightness change image, c) obtaining a small area fill image by filling a closed area whose area is not larger than a predetermined area in the lightness change binary image, d) obtaining a thin line image by performing a thinning processing on the small area fill image, e) obtaining a corrected thin line image by deleting a small projection in the thin line image, f) obtaining a colony fill image by filling a closed area in the corrected thin line image, g) obtaining a colony boundary image representing a boundary of a cell colony from an image obtained by taking a logical product of the colony fill image and the lightness change binary image or another lightness change binary image obtained from the colony image by another method, and h) specifying an area of a cell colony on the basis of the colony boundary image.

In another preferred embodiment of the present invention, the lightness change image is an image in which a value of a pixel at each position is a value which corresponds to a difference between an average of values of pixels in the colony image, which are located within a first distance from the each position, and an average of values of pixels located away from the each position farther than the first distance and nearer than a second distance. The lightness change binary image is an image representing a linear area which is adjacent to the inside of a strip-like area appearing around a cell colony along a boundary of the strip-like area. A logical product of the colony fill image and the another lightness change binary image is obtained in the operation g), and the another lightness change binary image is an image which is obtained by binarizing the lightness change image with a threshold value different from that used for the lightness change binary image and represents a linear area which is adjacent to the outside of the strip-like area along the boundary of the strip-like area.

Preferably, the operation part further performs performing a thickening processing on at least one of the colony fill image and the another lightness change binary image, before the operation g). Still preferably, the operation part further performs performing a thickening processing on the lightness change binary image, between the operation b) and the operation c).

In still another preferred embodiment of the present invention, an apparatus includes an image pickup part for picking up an image of a cell colony, to acquire a colony image, an operation part for specifying an area of the cell colony in the colony image by performing a computation processing, and an output part for outputting the area which is specified. The operation part performs a) obtaining a colony binary image by binarizing the colony image with a threshold value which separates an area of a cell colony from the other area, b) obtaining a peripheral binary image by binarizing the colony image with a threshold value which separates a strip-like area appearing around the cell colony from the other area, c) performing a thickening processing on at least one of the colony binary image and the peripheral binary image, d) obtaining an initial boundary image by taking a logical product of the colony binary image and the peripheral binary image which are obtained after the operation c), and e) specifying an area of a cell colony on the basis of the initial boundary image.

In another preferred embodiment of the present invention, a thickening processing is performed on the colony binary image and the peripheral binary image in the operation c).

In still another preferred embodiment of the present invention, the operation part further performs performing a shading compensation on the colony image, before the operation a) and the operation b).

The present invention is also intended for a cell colony area specifying method for specifying an area of a cell colony in a colony image, and still also intended for a computer-readable recording medium for recording therein a program to cause a computer to specify an area of a cell colony in a colony image.

These and other objects, features, aspects and advantages of the present invention will become more apparent from the following detailed description of the present invention when taken in conjunction with the accompanying drawings.

DESCRIPTION OF EMBODIMENTS

Figure 1:
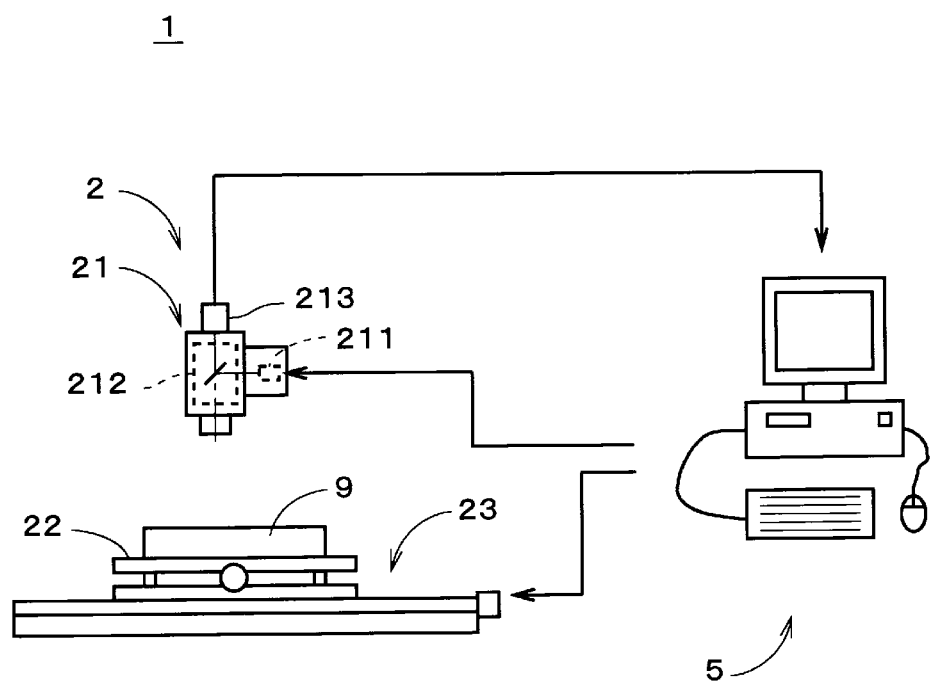
FIG. 1 is a view showing a configuration of a cell colony area specifying apparatus.

FIG. 1 is a view showing a configuration of a cell colony area specifying apparatus 1 (hereinafter, referred to simply as an "area specifying apparatus") in accordance with one preferred embodiment of the present invention. The area specifying apparatus 1 picks up an image of a cell colony in a culture vessel 9, to thereby specify an area of the cell colony in the image. The area specifying apparatus 1 includes an image pickup part 2, a computer 5 which controls a general operation of the area specifying apparatus 1 and implements an image processing described later.

The image pickup part 2 has an image pickup device 21 for picking up an image of the culture vessel 9, to thereby acquire a grayscale image, a stage 22 on which the culture vessel 9 is placed, and a stage driving part 23 for transferring the stage 22 relatively to the image pickup device 21. The image pickup device 21 has a lighting part 211 for emitting an illumination light, an optical system 212 which guides the illumination light to the culture vessel 9 and receives a light from the culture vessel 9, and an area sensor 213 for converting an image which is formed by the optical system 212 into an electrical signal. The stage driving part 23 is constituted of a ball screw, a guide rail, a motor, and the like, and the computer 5 controls the stage driving part 23 and the image pickup device 21, to thereby pick up an image of a partial area on the culture vessel 9.

Figure 2:
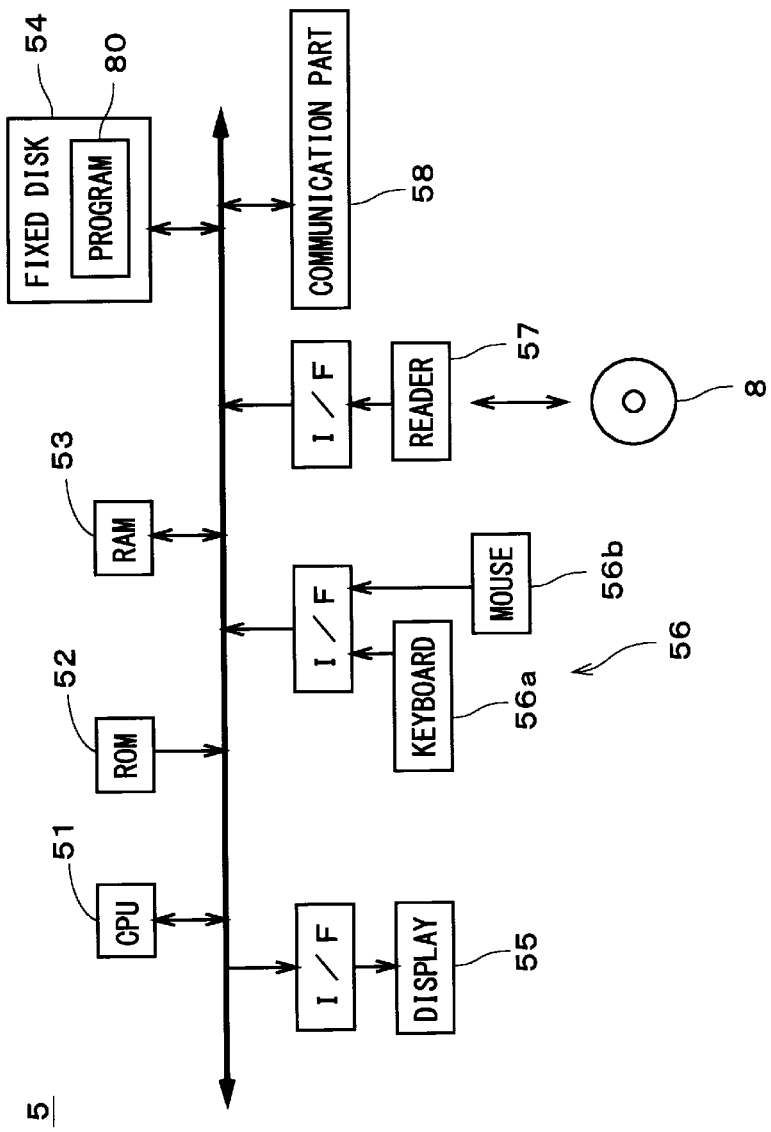
FIG. 2 is a view showing a constitution of a computer.

FIG. 2 is a view showing a constitution of the computer 5. The computer 5 has a general structure of computer system including a CPU 51 for performing various computations, a ROM 52 for storing a basic program, and a RAM 53 for storing various information. The computer 5 further includes a fixed disk 54 for storing information, a display 55 for displaying various information such as images and the like, a keyboard 56a and a mouse 56b (hereinafter, generally referred to as an "input part 56") for receiving an input from an operator, a reader 57 for reading information out from a computer-readable recording medium 8, such as an optical disk, a magnetic disk, a magneto-optic disk, or the like, and a communication part 58 for transmitting and receiving signals to/from other constituent elements of the area specifying apparatus 1.

In the computer 5, a program 80 is read out from the recording medium 8 through the reader 57 in advance and stored in the fixed disk 54. The CPU 51 executes the computations according to the program 80 while using the RAM 53 and the fixed disk 54.

Figure 3:
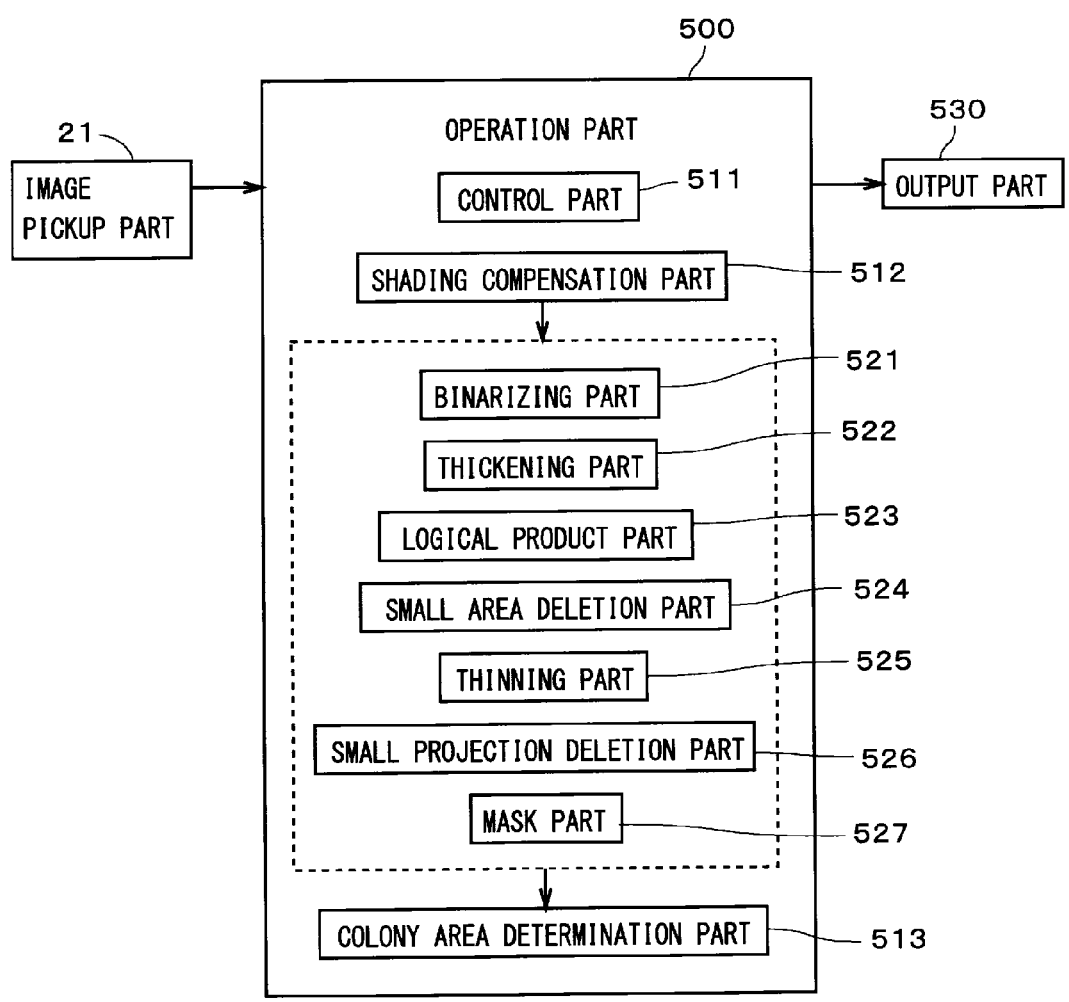
FIG. 3 is a block diagram showing a functional constitution in the cell colony area specifying apparatus.

FIG. 3 is a block diagram showing a functional constitution in the area specifying apparatus 1. FIG. 3 shows the functional constitution implemented by the CPU 51, the ROM 52, the RAM 53, the fixed disk 54, and the like of the computer 5, as an operation part 500. The operation part 500 includes, as its functions, a control part 511, a shading compensation part 512, a binarizing part 521, a thickening part 522, a logical product part 523, a small area deletion part 524, a thinning part 525, a small projection deletion part 526, a mask part 527, and a colony area determination part 513. Some or all of the functions of the operation part 500 may be constructed as hardwares. An output part 530 is a part for outputting a specified colony area to a user or any of other apparatuses, which corresponds to the display 55 and/or the communication part 58.

FIGS. 4 to 7 are flowcharts showing an exemplary operation flow of the area specifying apparatus 1. In the following description, acquisition of an image and processing on the image are exactly acquisition of image data and processing on the image data.

Figure 4:
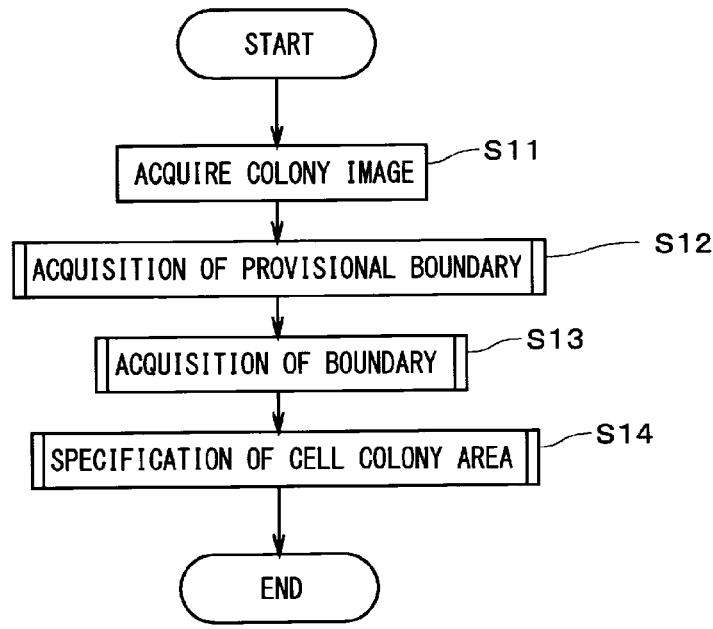
FIG. 4 is a flowchart showing an operation flow of the apparatus.

First, the image pickup part 2 picks up an image of a cell colony in the culture vessel 9, to thereby acquire the image (FIG. 4: Step S11). Hereinafter, the acquired image will be referred to as a "colony image". Through a computation processing by the operation part 500, an area of the cell colony in the colony image is specified and the specified area is outputted from the output part 530. In the processing by the operation part 500, a provisional boundary of the cell colony is acquired from the colony image (Step S12), and an accurate boundary is acquired from this provisional boundary (Step S13). After that, on the basis of the acquired boundary, a cell colony area is specified (Step S14).

Figure 5:
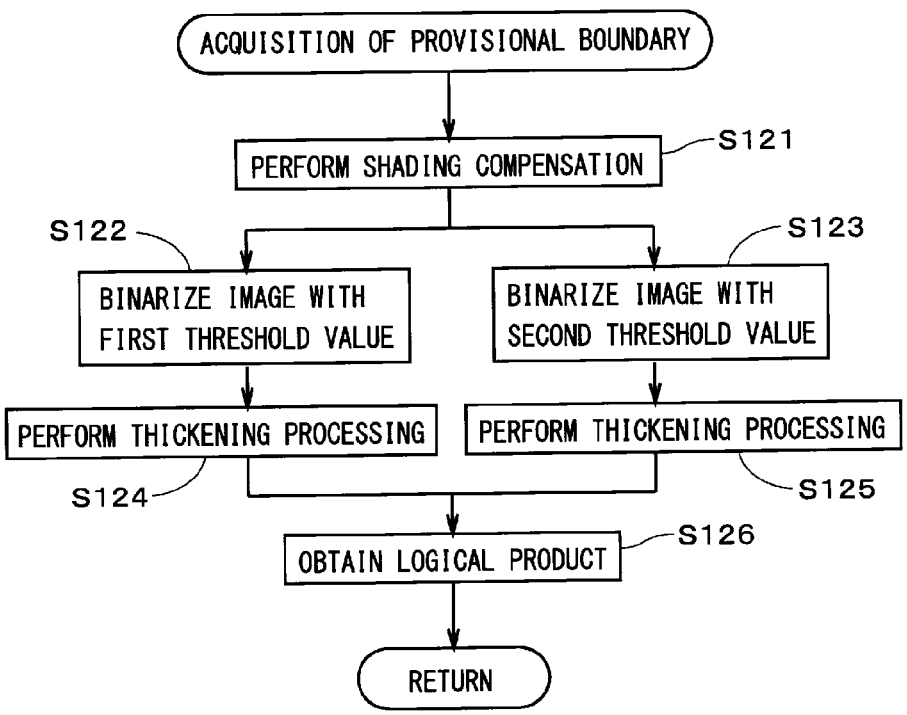
FIG. 5 is a flowchart showing an operation flow for acquisition of a provisional boundary.
Figure 8:
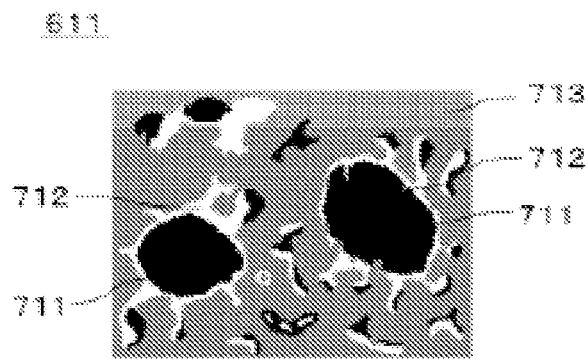
FIG. 8 is a view showing a colony image.

FIG. 5 is a flowchart showing an operation flow for acquisition of an image provisionally representing the boundary of the cell colony from the colony image in Step S12. The shading compensation part 512 performs a shading compensation on the colony image (Step S121). With this processing, an overall density irregularity of the image is reduced and the boundary of the cell colony can be more accurately acquired in the later process. FIG. 8 is a view showing an exemplary colony image 611 after being subjected to the shading compensation. In FIG. 8, the grayscale is shown in a simplified manner. In the example of FIG. 8, an area 711 of each actual cell colony is dark, and a bright strip-like area 712 appears around the cell colony. Other areas 713 have density influenced by other objects and have a lightness almost between the lightness of the cell colony area 711 and that of the strip-like area 712. The boundary of the cell colony to be extracted is a boundary between the cell colony area 711 and the strip-like area 712.

The lightnesses of these areas are inverted by a change of the imaging environment. In this case, after inverting the brightness in advance, the following processing is performed on the colony image. Alternatively, in the following processes, the processing with regard to the brightness is inverted.

Figure 9A:
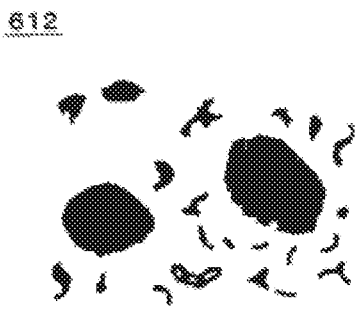
FIG. 9A is a view showing a colony binary image.
Figure 9B:
FIG. 9B is a view showing a peripheral binary image.

The colony image after being subjected to the shading compensation is binarized by the binarizing part 521 with a first threshold value which separates the cell colony area from other areas. Herein, a pixel value of "1" is given to the cell colony area. Hereinafter, the obtained binary image will be referred to as a "colony binary image" (Step S122). FIG. 9A is a view showing an exemplary colony binary image 612. On the other hand, the colony image after being subjected to the shading compensation is also binarized by the binarizing part 521 with a second threshold value which separates the strip-like area 712 appearing around the cell colony from other areas. Herein, a pixel value of "1" is given to the strip-like area. Hereinafter, the obtained binary image will be referred to as a "peripheral binary image" (Step S123). FIG. 9B is a view showing an exemplary peripheral binary image 613.

Figure 10A:
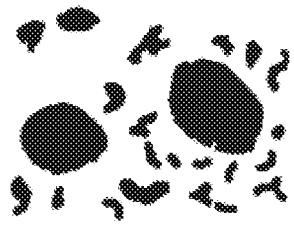
FIG. 10A is a view showing the colony binary image after being thickened.
Figure 10B:
FIG. 10B is a view showing the peripheral binary image after being thickened.

The threshold values used for obtaining the colony binary image 612 and the peripheral binary image 613 are determined by using a standard deviation or a histogram of the lightness distribution of the colony image. As shown in FIGS. 10A and 10B, the thickening processing is performed on the colony binary image 612 and the peripheral binary image 613 by the thickening part 522 (Steps S124 and S125). The thickening processing may be performed on only either one of the colony binary image 612 and the peripheral binary image 613.

Figure 11A:
FIG. 11A is a view showing a manner for taking a logical product.
Figure 11B:
FIG. 11B is a view showing an initial boundary image.

The logical product part 523 obtains a logical product of the colony binary image 612 and the peripheral binary image 613 after the thickening processing, i.e., an overlapping area among the areas whose pixel value is "1" in both the images as shown in FIG. 11A, to thereby obtain an image 614 shown in FIG. 11B (Step S126). The image 614 is an image including at least parts of the boundary of the cell colony, which provisionally represents the boundary of the cell colony. Hereinafter, the image 614 will be referred to as an "initial boundary image". In a case where the thickening processing is performed on both the colony binary image 612 and the peripheral binary image 613 in Step S125, any positional difference of the boundary in the initial boundary image 614 is reduced.

Figure 6A:
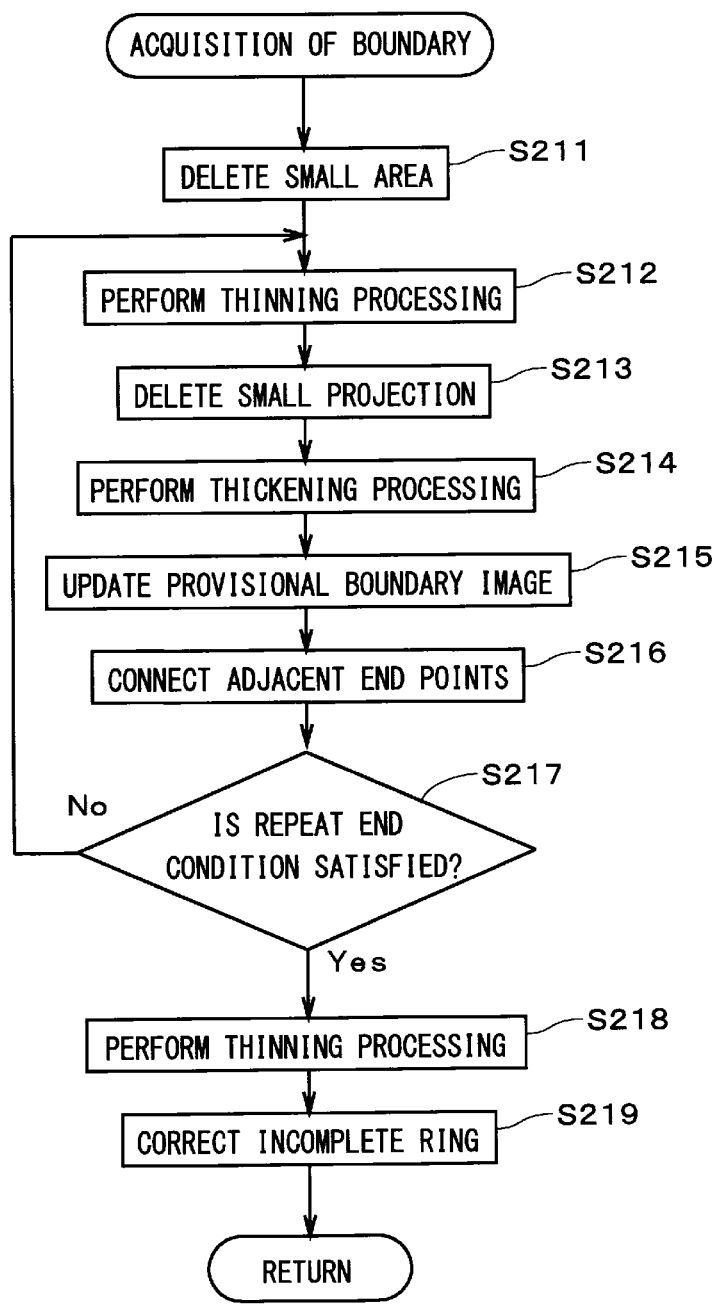
FIGS. 6A and 6B are flowcharts each showing an operation flow for acquisition of a boundary.
Figure 6B:
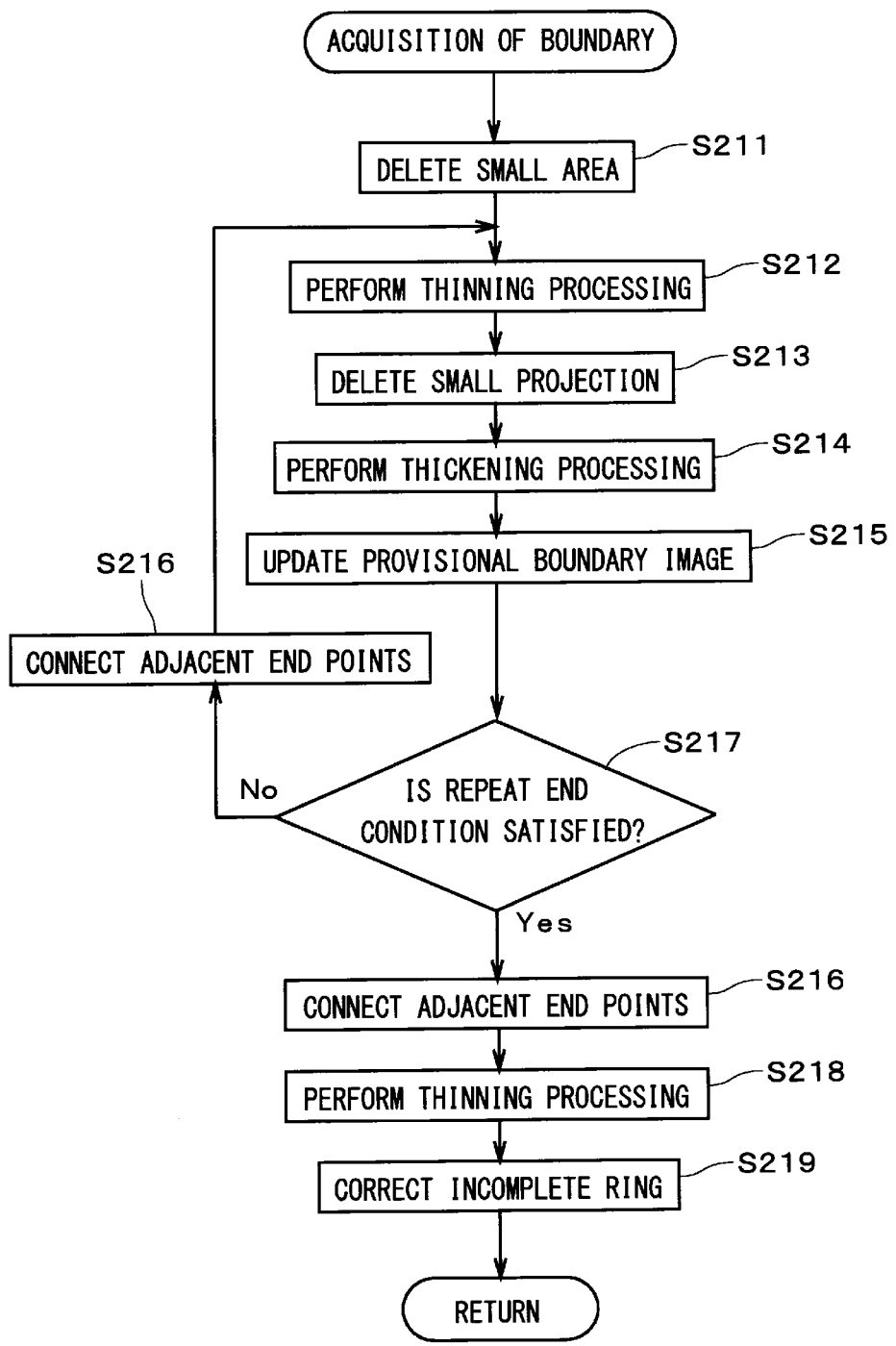
Figure 12:
FIG. 12 is a view showing a provisional boundary image.

FIGS. 6A and 6B are flowcharts each showing an operation flow for acquisition of an image representing a more accurate boundary of the cell colony, from the initial boundary image 614. First, the small area deletion part 524 deletes a small area whose area is not larger than a predetermined value, from the initial boundary image 614, to thereby obtain a provisional boundary image 621 shown in FIG. 12 (Step S211). This deletes an unnecessary area caused by dirts and/or noises. If there is a too large area such as a shadow of the vessel or the like, an area larger than a prescribed colony may be deleted in advance.

Figure 13:
FIG. 13 is a view showing a provisional boundary thin-line image.
Figure 14:
FIG. 14 is a view showing the provisional boundary thin-line image after being shaped.

The thinning part 525 performs a thinning processing on the provisional boundary image 621, to thereby acquire an image 622 shown in FIG. 13 (Step S212). Further, a thickening processing may be performed before the thinning processing. With this processing, very small dents and/or holes are removed, and the line after being subjected to the thinning processing is thereby smoothed. Hereinafter, the image 622 will be referred to a "provisional boundary thin-line image". In the provisional boundary thin-line image 622, very small projections each shorter than a predetermined length are deleted by the small projection deletion part 526, and the provisional boundary thin-line image 622 is thereby shaped as shown in FIG. 14 (Step S213). The concept of the very small projection may include a very small line existing solely, which is caused by dirts and/or noises.

Figure 15:
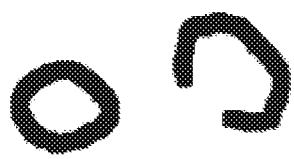
FIG. 15 is a view showing a mask image.
Figure 16A:
FIG. 16A is a view showing a manner for masking the initial boundary image.
Figure 16B:
FIG. 16B is a view showing an updated provisional boundary image.

The thickening part 522 performs the thickening processing on the provisional boundary thin-line image 622, to thereby acquire a mask image 623 shown in FIG. 15 (Step S214). The amount of thickening is determined in advance on the basis of an assumed length of break in the boundary. The mask part 527 masks the initial boundary image 614 shown in FIG. 12 with the mask image 623, as shown in FIG. 16A (Step S215). With this processing, an updated provisional boundary image 621 is obtained. As can be seen from the comparison between FIGS. 12 and 16B, in the updated provisional boundary image 621, some of the small areas appear, which have been deleted in Step S211 though these areas are parts of the boundary. In FIG. 16B, reference numeral "81" is given to the recovered small area.

Figure 17:
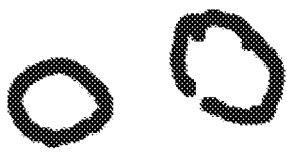
FIG. 17 is a view showing the provisional boundary image after being thickened.

Next, in the updated provisional boundary image 621, a processing where end points adjacent to each other are connected to each other is performed (Step S216). Though the connecting processing may be performed in various manners, in the present preferred embodiment, as shown in FIG. 17, the thickening part 522 performs the thickening processing on the provisional boundary image 621, to thereby connect the end points. In other words, the thickening part 522 serves as a connection part for connecting the adjacent end points. With this processing, the recovered small area 81 is connected to a boundary element adjacent thereto. As another connecting processing, a method in which adjacent end points are connected to each other with a straight line may be adopted.

Herein, the control part 511 checks whether a predetermined repeat end condition is satisfied or not (Step S217). The repeat end condition is a condition used for determining whether or not the provisional boundary image 621 is an image which sufficiently represents the boundary of the cell colony. Preferably, as the repeat end condition, used is a condition that the provisional boundary image 621 obtained in Step S215 is coincident with the provisional boundary image 621 obtained after the previous Step S215. This condition is equivalent to a condition that the provisional boundary image 621 obtained in Step S216 is coincident with the provisional boundary image 621 obtained after the previous Step S216. As another repeat end condition, preferably, adopted is a condition that the number of executions of Step S215 or Step S216 reaches a predetermined number.

Figure 18:
FIG. 18 is a view showing a provisional boundary thin-line image.
Figure 19:
FIG. 19 is a view showing the provisional boundary thin-line image after being shaped.
Figure 20:
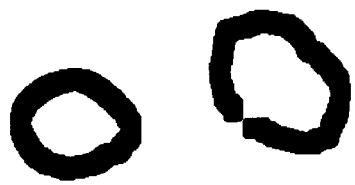
FIG. 20 is a view showing a mask image.

In the first Step S217, since there is no previous Step S215, it is determined that the repeat end condition is not satisfied, and the process goes back to Step S212. Then, the thinning part 525 performs the thinning processing on the provisional boundary image 621 shown in FIG. 17, to thereby obtain the provisional boundary thin-line image 622 shown in FIG. 18 (Step S212). As shown in FIG. 19, the small projection deletion part 526 deletes a small projection from the provisional boundary thin-line image 622 (Step S213), and as shown in FIG. 20, the thickening part 522 performs the thickening processing on the provisional boundary thin-line image 622, to thereby obtain the mask image 623 (Step S214).

Figure 21:
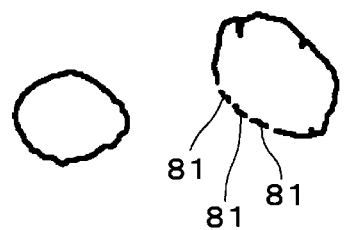
FIG. 21 is a view showing an updated provisional boundary image.
Figure 22:
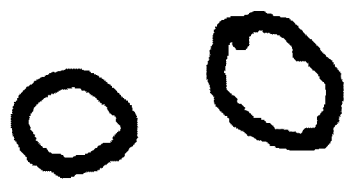
FIG. 22 is a view showing the provisional boundary image after being thickened.

Further, the mask part 527 masks the initial boundary image 614 with the mask image 623, to thereby obtain the provisional boundary image 621 in which more small areas 81 are recovered as shown in FIG. 21 (Step S215), and the thickening part 522 connects the adjacent end points to each other as shown in FIG. 22 (Step S216).

Figure 23:
FIG. 23 is a view showing a provisional boundary thin-line image.

Since the provisional boundary image 621 shown in FIG. 16B is not coincident with the provisional boundary image 621 shown in FIG. 21, the control part 511 determines that the repeat end condition is not satisfied (Step S217) and the process goes back to Step S212. With this processing, the provisional boundary thin-line image 622 shown in FIG. 23 is obtained (Step S212), and a corrected provisional boundary thin-line image 622 shown in FIG. 24 is obtained (Step S213).

Figure 24:
FIG. 24 is a view showing the provisional boundary thin-line image after being shaped.

After that, the thickening processing is performed on the provisional boundary thin-line image 622 shown in FIG. 24, to thereby obtain the mask image 623 (Step S214), and the initial boundary image 614 is masked with the mask image 623, to thereby obtain the updated provisional boundary image 621 like that in FIG. 21 (Step S215). Then, as shown in FIG. 22, the end points are connected to each other (Step S216). Since the provisional boundary image 621 obtained in Step S215 is coincident with the provisional boundary image 621 obtained in the previous Step S215, the control part 511 determines that no more repeating process is needed, and the process goes to Step S218.

Further, since whether the repeating process is needed or not can be determined in Step S215, as shown in FIG. 6B, whether the repeat end condition is satisfied or not may be checked after Step S215 (Step S217). In the flowchart of FIG. 6B, when the repeat end condition is not satisfied, connection of the adjacent end points to each other (Step S216) is performed and then the process goes back to Step S212. When the repeat end condition is satisfied, connection of the adjacent end points to each other (Step S216) is performed and then the process goes to Step S218.

The thinning part 525 performs the thinning processing on the final provisional boundary image 621 (Step S218). Hereinafter, the obtained image will be referred to as a "boundary thin-line image". Since the provisional boundary thin-line image 622 shown in FIG. 24, however, is already obtained in the previous Step S211 depending on the repeat end condition, Step S218 is omitted and preparation for the next operation is made, with this provisional boundary thin-line image 622 being regarded as the boundary thin-line image after Steps S216 and S218.

Next, in the boundary thin-line image, the boundary of the cell colony which is not represented as a complete closed loop is forcedly repaired (Step S219). In other words, an incomplete closed loop is forcedly closed. Specifically, in a case where a ratio of a distance between both ends of a line which is not annular to a length of the line is not larger than a predetermined value, connection of both the ends of the line is performed. Completion of the closed loop is achieved, for example, by increasing the amount of thickening in the thickening part 522. In this case, the thickening part 522 serves as a loop repair part. Completion of the closed loop may be performed by simply connecting both the ends with a straight line. When the boundary of the cell colony has been sufficiently extracted in Step S217 or S218, Step S219 may be omitted.

Figure 7:
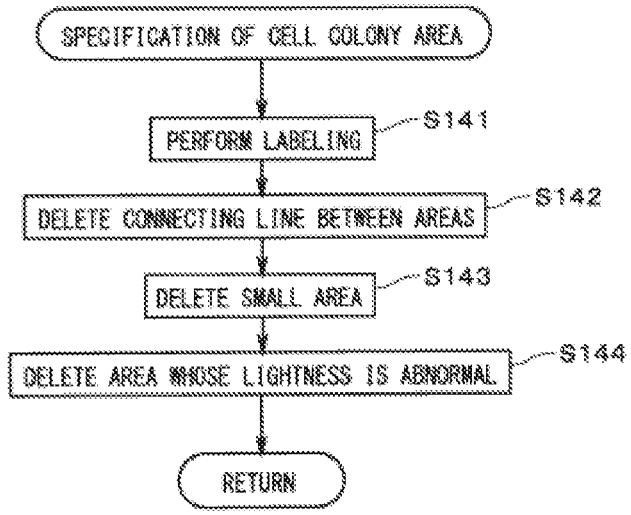
FIG. 7 is a flowchart showing an operation flow for specification of a cell colony area.
Figure 25:
FIG. 25 is a view showing a specified area of a cell colony.

FIG. 7 is a flowchart showing an operation flow of the processing performed by the colony area determination part 513 in Step S14 of FIG. 4. First, labeling of a closed area in the boundary thin-line image is performed, and each closed area surrounded by a line thereby becomes distinguishable as shown in FIG. 25 (Step S141). With this processing, an area of the cell colony (exactly, a candidate for the area of the cell colony, since there are further subsequent operations) is specified. Furthermore, as necessary, various correcting operations are performed. In a case, for example, where there remains a line connecting a closed area and another closed area, the line is deleted (Step S142).

The closed area whose area is smaller than a predetermined area is deleted from the image since the closed area is not appropriate as the cell colony area (Step S143). Further, if there is a too large closed area, such an area may be also deleted. An appropriate range of area is determined in advance from the assumed size of the cell colony. By using the circularity of the closed area, a candidate area of the cell colony may be selected.

Further, in the example of FIG. 8, since the cell colony appears darkly in the image, an area whose lightness is abnormal in the colony image is excluded from the cell colony area (Step S144). Specifically, in the colony image, in a case where a difference in average lightness between the inside of the closed area surrounded by the line in the boundary thin-line image and a peripheral portion of the closed area, i.e., an area 713 outside the strip-like area 712 is not larger than a predetermined value, it is determined that the area is not the cell colony area. By executing Steps S143 and S144, the cell colony area can be specified more accurately.

As described above, in the colony image, in some cases, the strip-like area whose lightness is different from that of the cell colony appears around the cell colony, and further a boundary between this strip-like area and the cell colony area is blurred. In the area specifying apparatus 1, a binary image including the cell colony area and another binary image including the strip-like area are generated by using two threshold values, and the thickening processing is performed on at least one of these binary images, to thereby obtain a common area of these binary images as the initial boundary image. In an image in which the boundary of the cell colony is blurred and widened, by using the initial boundary image which is obtained as above, the effect of the width of the boundary can be removed by thinning. As a result, it is possible to specify the cell colony area easily and efficiently.

Further, even when an area which corresponds to the boundary is broken in the initial boundary image, by repeating the process in which the thickening processing is performed on the provisional boundary thin-line image to generate the mask image, the broken portions can be gradually connected easily. Also with this operation, it is possible to specify the cell colony area easily and efficiently.

Since the adjacent end points are forcedly connected to each other when the repair of the broken portions is sufficiently performed by using the mask image, the boundary of the cell colony can be acquired with higher accuracy.

Figure 26:
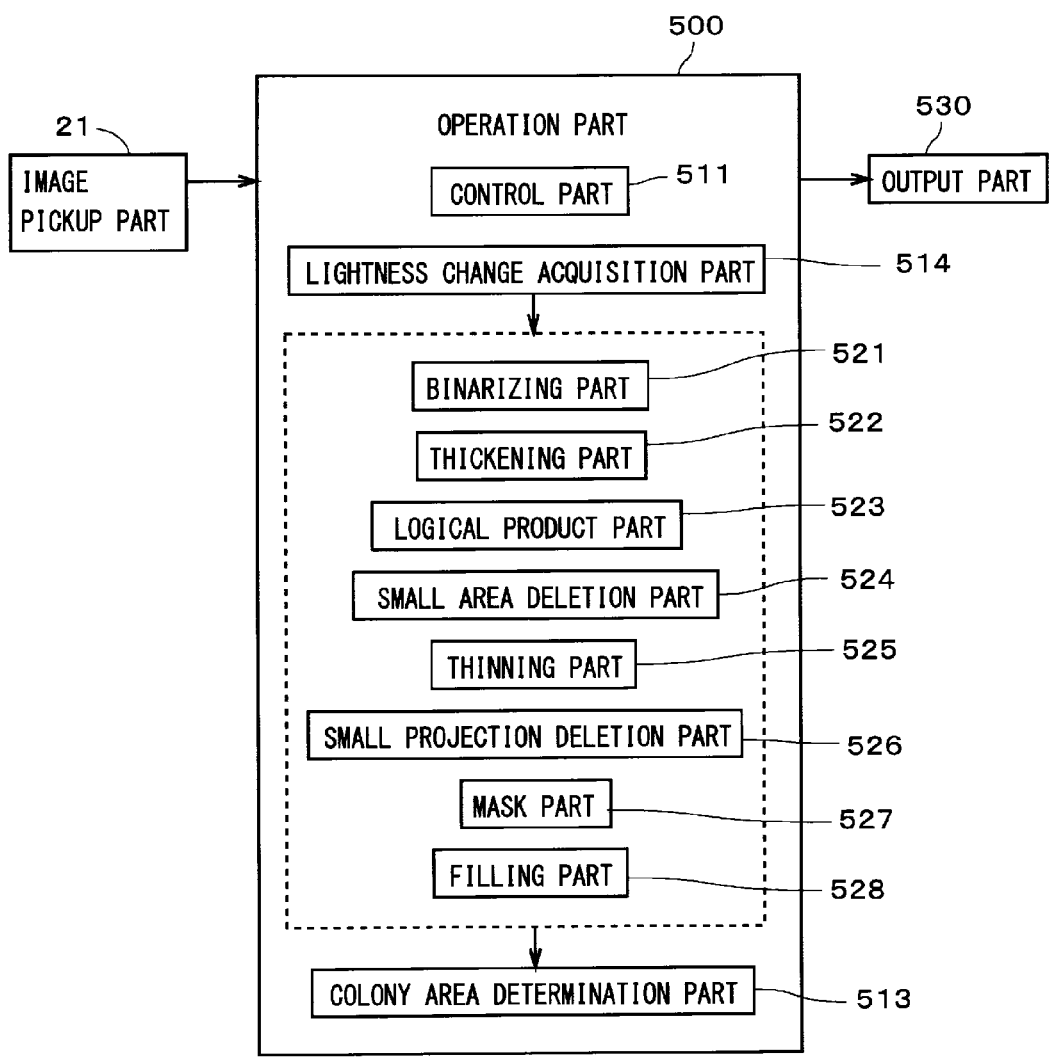
FIG. 26 is a block diagram showing a functional constitution in the cell colony area specifying apparatus.

FIG. 26 is a block diagram showing a functional constitution of an operation part 500 in another exemplary operation of the area specifying apparatus 1. In the functional constitution of FIG. 26, the shading compensation part 512 of FIG. 3 is replaced by a lightness change acquisition part 514 and a filling part 528 is additionally provided. The constituent elements other than these are identical to those in FIG. 3. Also in another exemplary operation described below, Steps S11 to S14 of FIG. 4 are executed. Operations in Steps S11, S13, and S14 are the same as those described above. The operation of Step S12 is replaced by an operation shown in FIGS. 27A and 27B.

In Step S12 in which the initial boundary image representing the initial provisional boundary of the cell colony is acquired, first, the lightness change acquisition part 514 acquires a lightness change image representing a difference in lightness between each position of the colony image and its periphery (Step S311). The lightness change image may be acquired by any of various methods. In the present preferred embodiment, adopted is a simple method in which a relation between a distance from each position and the average lightness is used and an image having a large amount of information is acquired.

Specifically, first, one pixel in the colony image is selected. A first average value which is an average of values of pixels located within a predetermined first distance from the selected pixel is obtained. Further, a second distance which is larger than the first distance is determined in advance, and a second average value which is an average of values of pixels located away from the selected pixel farther than the first distance and nearer than the second distance is obtained. Then, a value which corresponds to a signed difference between the first average value and the second average value is given as a value at the position of the selected pixel in the lightness change image. By repeating the above process while changing the selected pixel, the lightness change image is acquired. The "value which corresponds to the signed difference" is, for example, a value obtained by converting the signed difference into a value within a pixel value range from 0 to 255.

Figure 28:
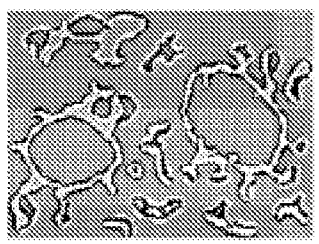
FIG. 28 is a view showing a lightness change image.

FIG. 28 is a view showing an exemplary lightness change image 641. In FIG. 28, the grayscale of the image is shown in a simplified manner. In the lightness change image 641, in principle, at a boundary between a bright area and a dark area in the colony image, the side of the bright area becomes bright along the boundary and the side of the dark area becomes dark along the boundary. An area in which the variation in density is small, such as the inside of the bright area, the inside of the dark area, the inside of other areas, or the like is halftone (gray).

Specifically, at a boundary between the dark area (see reference numeral 711 in FIG. 8) which corresponds to the cell colony and the bright strip-like area (see reference numeral 712 in FIG. 8) therearound, the side of the cell colony becomes dark along the boundary and the side of the strip-like area becomes bright along the boundary. At a boundary between the strip-like area and the other halftone area, the side of the strip-like area becomes bright along the boundary and the side of the halftone area becomes dark along the boundary.

Figure 29A:
FIG. 29A is a view showing a first lightness change binary image.

The lightness change image 641 is binarized by the binarizing part 521 with the first threshold value by which a bright area is appropriately extracted (Step S312). With this processing, a pixel value of "1" is given to the bright area. Hereinafter, this binary image will be referred to as a "first lightness change binary image". FIG. 29A shows an exemplary first lightness change binary image 642. The first lightness change binary image 642 represents a liner area adjacent to the inside of the strip-like area along the boundary of the strip-like area appearing around the cell colony.

Figure 29B:
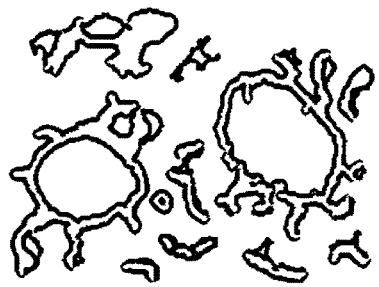
FIG. 29B is a view showing a second lightness change binary image.

The lightness change image 641 is binarized by the binarizing part 521 with the second threshold value by which a dark area is appropriately extracted, in other words, with a value on the darker side than the first threshold value (Step S313). With this processing, a pixel value of "1" is given to the dark area. Hereinafter, this binary image will be referred to as a "second lightness change binary image". FIG. 29B shows an exemplary second lightness change binary image 643. The second lightness change binary image 643 represents a liner area adjacent to the outside of the strip-like area along the boundary of the strip-like area appearing around the cell colony. Therefore, in the second lightness change binary image 643, a substantial double ring appears around the cell colony.

Figure 30A:
FIG. 30A is a view showing the first lightness change binary image after being thickened.
Figure 30B:
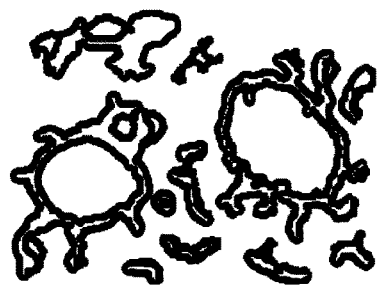
FIG. 30B is a view showing the second lightness change binary image after being thickened.

As shown in FIGS. 30A and 30B, the thickening part 522 performs the thickening processing on the first lightness change binary image 642 and the second lightness change binary image 643 (Steps S314 and S315). These thickening processings may be omitted.

Figure 31:
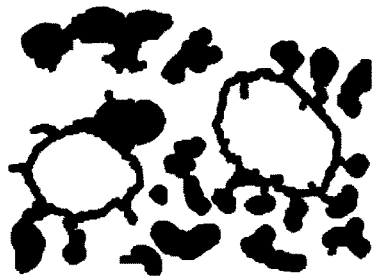
FIG. 31 is a view showing a small area fill image.
Figure 32:
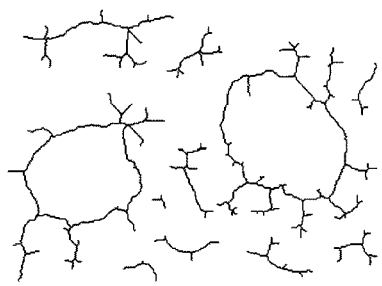
FIG. 32 is a view showing a thin line image.
Figure 33:
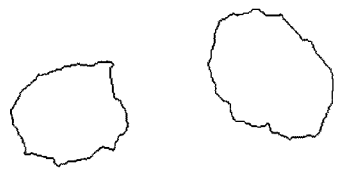
FIG. 33 is a view showing a corrected thin line image.

The filling part 528 fills a closed area whose area is not larger than a predetermined area in the first lightness change binary image 642 (Step S316). Hereinafter, the image in which the small area is filled will be referred to as a "small area fill image". FIG. 31 shows an exemplary small area fill image 644. The thinning part 525 performs the thinning processing on the small area fill image 644, to thereby obtain a thin line image 645 shown in FIG. 32 (Step S317). The small projection deletion part 526 deletes a small projection in the thin line image 645, to thereby obtain a thin line image 646 shown in FIG. 33 (Step S318). Hereinafter, the thin line image 646 will be referred to as a "corrected thin line image".

In the binarization of the lightness change image 641 in Step S312, used is the first threshold value by which a line which corresponds to a bright strip-like area around the cell colony can be extracted almost surely. For this reason, in the image obtained by filling and thinning the first lightness change binary image 642, a line surrounding the cell colony appears with high probability.

Figure 34:
FIG. 34 is a view showing a colony fill image.

The filling part 528 fills a closed area in the corrected thin line image 646, to thereby obtain an image 647 shown in FIG. 34 (Step S319). An outer edge portion of the filled area is presumed to cover the boundary of the cell colony. Hereinafter, the image 647 will be referred to as a "colony fill image".

Figure 35A:
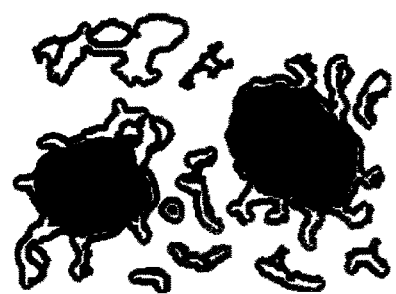
FIG. 35A is a view showing a manner for taking a logical product.
Figure 35B:
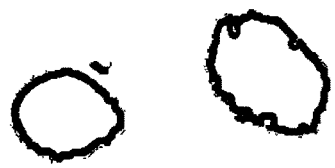
FIG. 35B is a view showing a colony boundary image.

Next, as shown in FIG. 35A, the logical product part 523 takes a logical product of the colony fill image 647 and the second lightness change binary image 643 shown in FIG. 30B, to thereby obtain an image 651 shown in FIG. 35B (Step S321). A line appearing in the second lightness change binary image 643 is located on the side of the dark area along the boundary between the bright area and the dark area. In other words, the line of the second lightness change binary image 643 appears inside the boundary of the cell colony or outside the bright strip-like area around the cell colony. For this reason, by taking the logical product of the colony fill image 647 and the second lightness change binary image 643, only an area located almost along the boundary of the cell colony can be obtained with high probability. Hereinafter, the image 651 shown in FIG. 35B which is obtained by taking the logical product will be referred to as a "colony boundary image".

Figure 36:
FIG. 36 is a view showing a corrected colony boundary image.
Figure 37:
FIG. 37 is a view showing the colony boundary image after being thickened.
Figure 38:
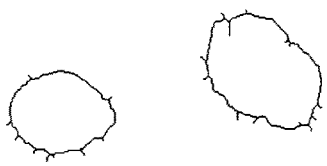
FIG. 38 is a view showing the colony boundary image after being thinned.

As shown in FIG. 36, the small area deletion part 524 deletes a very small area existing in the colony boundary image 651 (Step S322). As shown in FIG. 37, the thickening part 522 performs the thickening processing on the colony boundary image 651, to thereby smooth the shape of an annular area (Step S323). The thinning part 525 performs the thinning processing on the colony boundary image 651 shown in FIG. 37, to thereby acquire an image shown in FIG. 38 (Step S324), and the small projection deletion part 526 further deletes small projections in the thin line image as shown in FIG. 39 (Step S325), to thereby obtain a final colony boundary image 651 representing the boundary of the cell colony.

Figure 39:
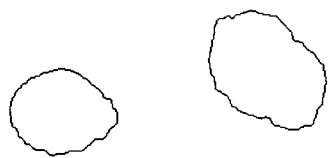
FIG. 39 is a view showing a final colony boundary image.

Though the annular line appears in the example of FIG. 39, actually in some cases, an incomplete annular line appears in the colony boundary image 651. Then, with the colony boundary image 651 as the initial boundary image representing an initial provisional boundary, the process goes to Step S13 of FIG. 4 and the operations shown in FIGS. 6A and 6B are performed. By performing this process, the broken annular line is corrected and the boundary thin-line image is thereby obtained. In a case where there exists no incomplete annular line as shown in FIG. 39, naturally, the repeating operation of Step S13 is immediately finished and the process goes to Step S14. Then, the process shown in FIG. 7 is performed and the cell colony area is thereby specified. When almost no incomplete annular line appears in the final colony boundary image, Step S13 may be omitted.

Figure 27A:
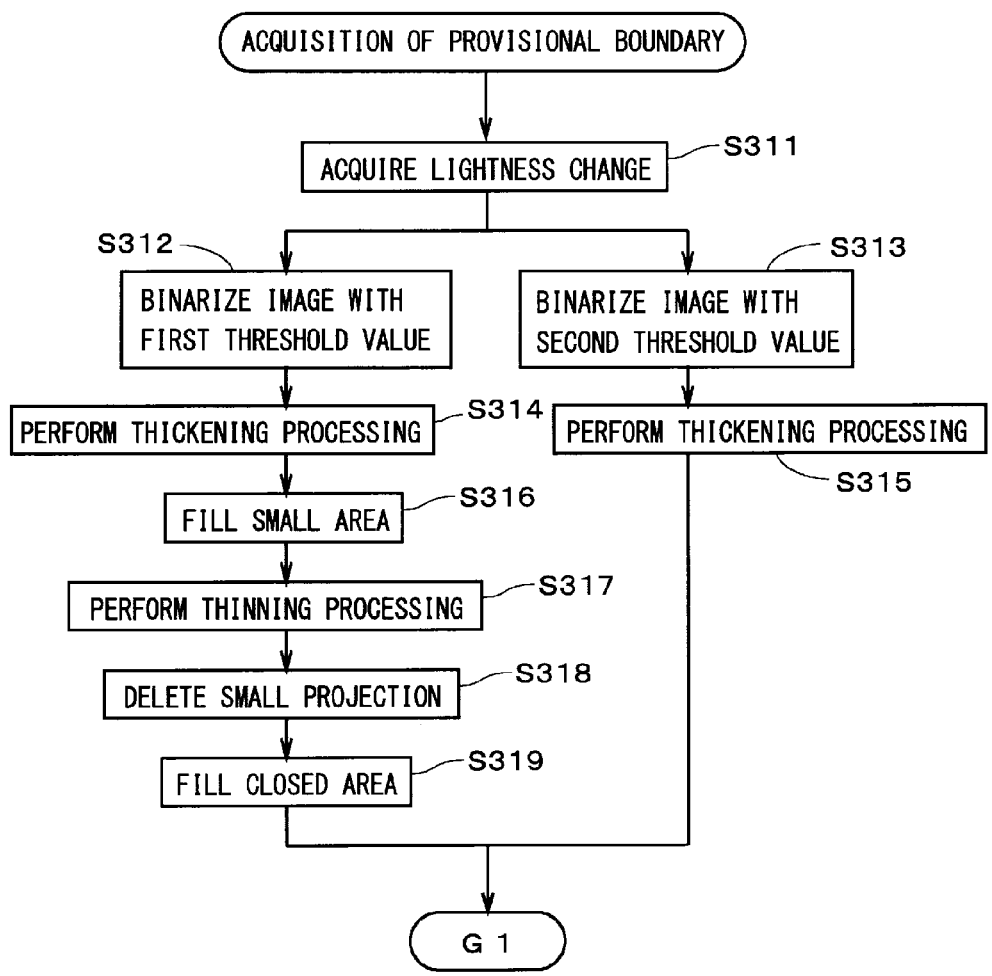
FIGS. 27A and 27B are flowcharts each showing an operation flow for acquisition of a provisional boundary.
Figure 27B:
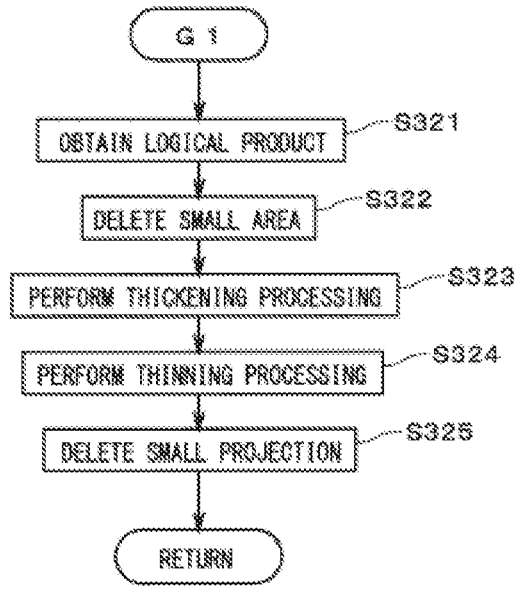

Though the image in which the bright line and the dark line appear between the bright area and the dark area in the colony image is used as the lightness change image 641 in the exemplary operation shown in FIGS. 27A and 27B, other images may be used only if the images represent the lightness change. A simple differential image, for example, may be used as the lightness change image.

In this case, by binarizing the lightness change image with a threshold value used for extracting an edge portion in the colony image, one lightness change binary image can be obtained. In the lightness change binary image, an edge of the bright strip-like area appearing around the cell colony is extracted as a substantial double ring. Then, without distinguishing between the first lightness change binary image and the second lightness change binary image in the process of FIG. 27A, the above one lightness change binary image is used instead of these lightness change binary images. In other words, in Step S321, a logical product of the colony fill image and the lightness change binary image used for generation of the colony fill image is obtained, to thereby acquire the colony boundary image from the logical product image.

In the area specifying apparatus 1, by using the lightness change image, the cell colony area can be appropriately specified without performing the shading compensation. Further, by obtaining a logical product of the colony fill image obtained by filling the image obtained from the lightness change binary image by thinning the strip-like area appearing around the cell colony and the lightness change binary image (or the second lightness change binary image) almost representing the edge of the strip-like area, it is possible to specify the cell colony area easily and efficiently even in the image in which the boundary of the cell colony is blurred.

Particularly in the case where the first lightness change binary image and the second lightness change binary image are used, by controlling the first threshold value and the second threshold value, it is possible to easily obtain an appropriate colony fill image and an appropriate second lightness change binary image.

In order to surely obtain the overlap of the colony fill image and the lightness change binary image, the logical product image may be obtained after performing the thickening processing on the colony fill image. It is preferable to perform the thickening processing on at least one of the colony fill image and the lightness change binary image. Further, in the thickening processing performed on the colony fill image and/or the lightness change binary image, by controlling the amount of thickening, it is possible to perform a fine control of the boundary position in the colony boundary image.

In the area specifying apparatus 1, in Step S316, before filling the small area of the (first) lightness change binary image, the thickening processing of Step S314 is performed. It is thereby possible to reduce the breaks of the line appearing around the cell colony.

The area specifying apparatus 1 may be changed in various manners.

The repair of the breaks in the boundary in Step S13, for example, can be used for the initial boundary image obtained by any of other methods. Further, by using the initial boundary image obtained in Step S12, the final area of the cell colony may be specified by any of other methods.

The image acquired by the image pickup part 2 may be a monochrome image or a color image. The colony image is generated from an original image through various preprocessings. In the image pick-up method, a reflected light from the culture vessel 9 may be used or a transmission light may be used. In the area specifying apparatus 1, the stage driving part 23 may be omitted.

The functions of the operation part 500 may be implemented by a plurality of computers. The program 80 can be introduced in the computer through various media.

The configurations of the above-described preferred embodiment and variations may be appropriately combined as long as there are no mutual inconsistencies.

While the invention has been shown and described in detail, the foregoing description is in all aspects illustrative and not restrictive. It is therefore understood that numerous modifications and variations can be devised without departing from the scope of the invention.

REFERENCE SIGNS LIST

1 Cell colony area specifying apparatus
5 Computer
21 Image pickup part
80 Program
500 Operation part
530 Output part
611 Colony image
612 Colony binary image
613 Peripheral binary image
614 Initial boundary image
621 Provisional boundary image
622 Provisional boundary thin-line image
623 Mask image
641 Lightness change image
642 First lightness change binary image
643 Second lightness change binary image
644 Small area fill image
645 Thin line image
646 Corrected thin line image
647 Colony fill image
651 Colony boundary image
712 Strip-like area
S11 to S14, S121 to S126, S141 to S144, S211 to S219, S311 to S319, S321 to S325 Step

The invention claimed is:

1. A cell colony area specifying apparatus for specifying an area of a cell colony in a colony image representing said cell colony, comprising:
an image pickup part for picking up an image of a cell colony, to acquire a colony image;
an operation part for specifying an area of said cell colony in said colony image by performing a computation processing; and
an output part for outputting said area which is specified,
wherein said operation part performs:
a) obtaining an initial boundary image provisionally representing a boundary of a cell colony from said colony image;
b) acquiring a provisional boundary image by deleting a small area from said initial boundary image;
c) obtaining a provisional boundary thin-line image by performing a thinning processing on said provisional boundary image;
d) obtaining a mask image by performing a thickening processing on said provisional boundary thin-line image;
e) obtaining an updated provisional boundary image by masking said initial boundary image with said mask image;
f) connecting end points adjacent to each other in said updated provisional boundary image;
g) checking whether a predetermined repeat end condition is satisfied or not after said operation e) and before or after said operation f), and returning to said operation c) after said operation f) when said repeat end condition is not satisfied, or obtaining a boundary thin-line image from an image obtained after said operation f) and going to an operation h) when said repeat end condition is satisfied; and h) specifying an area surrounded by a line in said boundary thin-line image, as an area of a cell colony.

2. The cell colony area specifying apparatus according to claim 1, wherein said repeat end condition is that the number of executions of said operation e) or said operation f) reaches a predetermined number or that an image obtained after said operation e) is coincident with an image obtained after a previous operation e).

3. The cell colony area specifying apparatus according to claim 1, wherein after said operation g) and before said operation h), when a ratio of a distance between both ends of a line which is not annular to a length of said line in said boundary thin-line image is not larger than a predetermined value, said operation part further performs connecting said both ends.

4. The cell colony area specifying apparatus according to claim 1, wherein when a difference in average lightness between the inside of the area surrounded by the line in said boundary thin-line image and a peripheral portion of said area is not larger than a predetermined value in said colony image, said operation h) includes determining said area not as an area of a cell colony.

5. A cell colony area specifying method for specifying an area of a cell colony in a colony image representing said cell colony, comprising:

a) obtaining an initial boundary image provisionally representing a boundary of a cell colony from a colony image;

b) acquiring a provisional boundary image by deleting a small area from said initial boundary image;

c) obtaining a provisional boundary thin-line image by performing a thinning processing on said provisional boundary image;

d) obtaining a mask image by performing a thickening processing on said provisional boundary thin-line image;

e) obtaining an updated provisional boundary image by masking said initial boundary image with said mask image;

f) connecting end points adjacent to each other in said updated provisional boundary image;

g) checking whether a predetermined repeat end condition is satisfied or not after said operation e) and before or after said operation f), and returning to said operation c) after said operation f) when said repeat end condition is not satisfied, or obtaining a boundary thin-line image from an image obtained after said operation f) and going to an operation h) when said repeat end condition is satisfied; and h) specifying an area surrounded by a line in said boundary thin-line image, as an area of a cell colony.

6. The cell colony area specifying method according to claim 5, wherein said repeat end condition is that the number of executions of said operation e) or said operation f) reaches a predetermined number or that an image obtained after said operation e) is coincident with an image obtained after a previous operation e).

7. The cell colony area specifying method according to claim 5, further comprising:

connecting both ends of a line which is not annular in said boundary thin-line image, after said operation g) and before said operation h), when a ratio of a distance between said both ends of said line to a length of said line is not larger than a predetermined value.

8. The cell colony area specifying method according to claim 5, wherein when a difference in average lightness between the inside of the area surrounded by the line in said boundary thin-line image and a peripheral portion of said area is not larger than a predetermined value in said colony image, said operation h) includes determining said area not as an area of a cell colony.

9. The cell colony area specifying method according to claim 5, wherein said operation a) comprising:

a1) obtaining a lightness change image representing a difference in lightness between each position in said colony image and its periphery;

a2) obtaining a lightness change binary image by binarizing said lightness change image;

a3) obtaining a small area fill image by filling a closed area whose area is not larger than a predetermined area in said lightness change binary image;

a4) obtaining a thin line image by performing a thinning processing on said small area fill image;

a5) obtaining a corrected thin line image by deleting a small projection in said thin line image;

a6) obtaining a colony fill image by filling a closed area in said corrected thin line image; and a7) obtaining a colony boundary image representing a boundary of a cell colony, as said initial boundary image, from an image obtained by taking a logical product of said colony fill image and said lightness change binary image or another lightness change binary image obtained from said colony image by another method.

10. The cell colony area specifying method according to claim 5, wherein said operation a) comprising:

a1) obtaining a colony binary image by binarizing said colony image with a threshold value which separates an area of a cell colony from the other area;

a2) obtaining a peripheral binary image by binarizing said colony image with a threshold value which separates a strip-like area appearing around said cell colony from the other area;

a3) performing a thickening processing on at least one of said colony binary image and said peripheral binary image; and a4) obtaining said initial boundary image by taking a logical product of said colony binary image and said peripheral binary image which are obtained after said operation a3).

11. A non-transitory computer-readable recording medium for recording therein a program to cause a computer to specify an area of a cell colony in a colony image representing said cell colony, said program being executed by said computer to cause said computer to perform:

a) obtaining an initial boundary image provisionally representing a boundary of a cell colony from a colony image;

b) acquiring a provisional boundary image by deleting a small area from said initial boundary image;

c) obtaining a provisional boundary thin-line image by performing a thinning processing on said provisional boundary image;

d) obtaining a mask image by performing a thickening processing on said provisional boundary thin-line image;

e) obtaining an updated provisional boundary image by masking said initial boundary image with said mask image;

f) connecting end points adjacent to each other in said updated provisional boundary image;

g) checking whether a predetermined repeat end condition is satisfied or not after said operation e) and before or after said operation f), and returning to said operation c) after said operation f) when said repeat end condition is not satisfied, or obtaining a boundary thin-line image from an image obtained after said operation f) and going to an operation h) when said repeat end condition is satisfied; and h) specifying an area surrounded by a line in said boundary thin-line image, as an area of a cell colony.

12. A cell colony area specifying apparatus for specifying an area of a cell colony in a colony image representing said cell colony, comprising:

an image pickup part for picking up an image of a cell colony, to acquire a colony image;

an operation part for specifying an area of said cell colony in said colony image by performing a computation processing; and an output part for outputting said area which is specified, wherein said operation part performs:

a) obtaining a lightness change image representing a difference in lightness between each position in said colony image and its periphery;

b) obtaining a lightness change binary image by binarizing said lightness change image;

c) obtaining a small area fill image by filling a closed area whose area is not larger than a predetermined area in said lightness change binary image;

d) obtaining a thin line image by performing a thinning processing on said small area fill image;

e) obtaining a corrected thin line image by deleting a small projection in said thin line image;

f) obtaining a colony fill image by filling a closed area in said corrected thin line image;

g) obtaining a colony boundary image representing a boundary of a cell colony from an image obtained by taking a logical product of said colony fill image and said lightness change binary image or another lightness change binary image obtained from said colony image by another method; and h) specifying an area of a cell colony on the basis of said colony boundary image.

13. The cell colony area specifying apparatus according to claim 12, wherein said lightness change image is an image in which a value of a pixel at each position is a value which corresponds to a difference between an average of values of pixels in said colony image, which are located within a first distance from said each position, and an average of values of pixels located away from said each position farther than said first distance and nearer than a second distance, said lightness change binary image is an image representing a linear area which is adjacent to the inside of a strip-like area appearing around a cell colony along a boundary of said strip-like area, a logical product of said colony fill image and said another lightness change binary image is obtained in said operation g), and said another lightness change binary image is an image which is obtained by binarizing said lightness change image with a threshold value different from that used for said lightness change binary image and represents a linear area which is adjacent to the outside of said strip-like area along said boundary of said strip-like area.

14. The cell colony area specifying apparatus according to claim 13, wherein said operation part further performs performing a thickening processing on at least one of said colony fill image and said another lightness change binary image, before said operation g).

15. The cell colony area specifying apparatus according to claim 13, wherein said operation part further performs performing a thickening processing on said lightness change binary image, between said operation b) and said operation c).

16. A cell colony area specifying apparatus for specifying an area of a cell colony in a colony image representing said cell colony, comprising:

an image pickup part for picking up an image of a cell colony, to acquire a colony image;

an operation part for specifying an area of said cell colony in said colony image by performing a computation processing; and an output part for outputting said area which is specified, wherein said operation part performs:

a) obtaining a colony binary image by binarizing said colony image with a threshold value which separates an area of a cell colony from the other area;

b) obtaining a peripheral binary image by binarizing said colony image with a threshold value which separates a strip-like area appearing around said cell colony from the other area;

c) performing a thickening processing on at least one of said colony binary image and said peripheral binary image;

d) obtaining an initial boundary image by taking a logical product of said colony binary image and said peripheral binary image which are obtained after said operation c); and e) specifying an area of a cell colony on the basis of said initial boundary image.

17. The cell colony area specifying apparatus according to claim 16, wherein a thickening processing is performed on said colony binary image and said peripheral binary image in said operation c).

18. The cell colony area specifying apparatus according to claim 16, wherein said operation part further performs performing a shading compensation on said colony image, before said operation a) and said operation b).

19. A cell colony area specifying method for specifying an area of a cell colony in a colony image representing said cell colony, comprising:

a) obtaining a lightness change image representing a difference in lightness between each position in a colony image and its periphery;

b) obtaining a lightness change binary image by binarizing said lightness change image;

c) obtaining a small area fill image by filling a closed area whose area is not larger than a predetermined area in said lightness change binary image;

d) obtaining a thin line image by performing a thinning processing on said small area fill image;

e) obtaining a corrected thin line image by deleting a small projection in said thin line image;

f) obtaining a colony fill image by filling a closed area in said corrected thin line image;

g) obtaining a colony boundary image representing a boundary of a cell colony from an image obtained by taking a logical product of said colony fill image and said lightness change binary image or another lightness change binary image obtained from said colony image by another method; and h) specifying an area of a cell colony on the basis of said colony boundary image.

20. The cell colony area specifying method according to claim 19, wherein said lightness change image is an image in which a value of a pixel at each position is a value which corresponds to a difference between an average of values of pixels in said colony image, which are located within a first distance from said each position, and an average of values of pixels located away from said each position farther than said first distance and nearer than a second distance, said lightness change binary image is an image representing a linear area which is adjacent to the inside of a strip-like area appearing around a cell colony along a boundary of said strip-like area, a logical product of said colony fill image and said another lightness change binary image is obtained in said operation g), and said another lightness change binary image is an image which is obtained by binarizing said lightness change image with a threshold value different from that used for said lightness change binary image and represents a linear area which is adjacent to the outside of said strip-like area along said boundary of said strip-like area.

21. The cell colony area specifying method according to claim 20, further comprising performing a thickening processing on at least one of said colony fill image and said another lightness change binary image, before said operation g).

22. The cell colony area specifying method according to claim 20, further comprising performing a thickening processing on said lightness change binary image, between said operation b) and said operation c).

23. A cell colony area specifying method for specifying an area of a cell colony in a colony image representing said cell colony, comprising:

a) obtaining a colony binary image by binarizing a colony image with a threshold value which separates an area of a cell colony from the other area;

b) obtaining a peripheral binary image by binarizing said colony image with a threshold value which separates a strip-like area appearing around said cell colony from the other area;

c) performing a thickening processing on at least one of said colony binary image and said peripheral binary image;

d) obtaining an initial boundary image by taking a logical product of said colony binary image and said peripheral binary image which are obtained after said operation c); and e) specifying an area of a cell colony on the basis of said initial boundary image.

24. The cell colony area specifying method according to claim 23, wherein a thickening processing is performed on said colony binary image and said peripheral binary image in said operation c).

25. The cell colony area specifying method according to claim 23, further comprising performing a shading compensation on said colony image, before said operation a) and said operation b).

26. A non-transitory computer-readable recording medium for recording therein a program to cause a computer to specify an area of a cell colony in a colony image representing said cell colony, said program being executed by said computer to cause said computer to perform:

a) obtaining a lightness change image representing a difference in lightness between each position in a colony image and its periphery;

b) obtaining a lightness change binary image by binarizing said lightness change image;

c) obtaining a small area fill image by filling a closed area whose area is not larger than a predetermined area in said lightness change binary image;

d) obtaining a thin line image by performing a thinning processing on said small area fill image;

e) obtaining a corrected thin line image by deleting a small projection in said thin line image;

f) obtaining a colony fill image by filling a closed area in said corrected thin line image;

g) obtaining a colony boundary image representing a boundary of a cell colony from an image obtained by taking a logical product of said colony fill image and said lightness change binary image or another lightness change binary image obtained from said colony image by another method; and h) specifying an area of a cell colony on the basis of said colony boundary image.

27. A non-transitory computer-readable recording medium for recording therein a program to cause a computer to specify an area of a cell colony in a colony image representing said cell colony, said program being executed by said computer to cause said computer to perform:

a) obtaining a colony binary image by binarizing a colony image with a threshold value which separates an area of a cell colony from the other area;

b) obtaining a peripheral binary image by binarizing said colony image with a threshold value which separates a strip-like area appearing around said cell colony from the other area;

c) performing a thickening processing on at least one of said colony binary image and said peripheral binary image;

d) obtaining an initial boundary image by taking a logical product of said colony binary image and said peripheral binary image which are obtained after said operation c); and e) specifying an area of a cell colony on the basis of said initial boundary image.

* * * * *